(12) United States Patent
Tokuhira et al.

(10) Patent No.: US 10,309,889 B2
(45) Date of Patent: Jun. 4, 2019

(54) EXHAUST GAS ANALYSIS SYSTEM, RECORDING MEDIUM RECORDED WITH PROGRAM FOR EXHAUST GAS ANALYSIS SYSTEM, AND EXHAUST GAS ANALYZING METHOD

(71) Applicant: HORIBA, Ltd., Kyoto (JP)

(72) Inventors: Masatsune Tokuhira, Kyoto (JP);
Jungo Okada, Kyoto (JP); Masahiro Higuchi, Kyoto (JP)

(73) Assignee: HORIBA, LTD., Kyoto (JP)

( * ) Notice: Subject to any disclaimer, the term of this patent is extended or adjusted under 35 U.S.C. 154(b) by 101 days.

(21) Appl. No.: 15/603,491

(22) Filed: May 24, 2017

(65) Prior Publication Data

US 2017/0343462 A1 Nov. 30, 2017

(30) Foreign Application Priority Data

May 24, 2016 (JP) .................................. 2016-103451

(51) Int. Cl.
*G01N 15/06* (2006.01)
*G01N 1/22* (2006.01)
(Continued)

(52) U.S. Cl.
CPC ....... *G01N 15/0618* (2013.01); *B01D 46/442* (2013.01); *F01N 3/021* (2013.01);
(Continued)

(58) Field of Classification Search
CPC ............. G01N 1/2252; G01N 15/0618; B01D 46/442; F01N 3/021; G01M 15/102; G01M 15/02
See application file for complete search history.

(56) References Cited

U.S. PATENT DOCUMENTS

2006/0236752 A1* 10/2006 Nakamura ......... G01N 33/0032
73/23.21
2014/0251031 A1 9/2014 Kumagai

FOREIGN PATENT DOCUMENTS

JP 2009-085842 A 4/2009
JP 2010139340 A 6/2010

OTHER PUBLICATIONS

EESR dated Nov. 2, 2017 issued for European Patent Application No. 17 172 430.5, 9 pages.

* cited by examiner

*Primary Examiner* — Bryan Bui
(74) *Attorney, Agent, or Firm* — Brooks Kushman P.C.

(57) ABSTRACT

An exhaust gas analysis system is adapted to include an exhaust gas circulation line through which exhaust gas flows, an exhaust gas collection line adapted to collect the exhaust gas from the exhaust gas circulation line and introduce the collected exhaust gas into an exhaust gas analysis device, a continuous analysis line adapted to, separately from the diluted exhaust gas collection line, collect the exhaust gas from the exhaust gas circulation line for continuous analysis, a continuous analyzer provided in the continuous analysis line, and an information processing unit adapted to, on the basis of an analysis result by the continuous analyzer at the time of the collection into the exhaust gas analysis device, determine whether a measurement result of the exhaust gas introduced into the exhaust gas analysis device falls within a preset range, or determine a measurement range used to measure the exhaust gas introduced into the exhaust gas analysis device.

7 Claims, 8 Drawing Sheets

(51) Int. Cl.
  *G01M 15/10*   (2006.01)
  *G01M 15/02*   (2006.01)
  *G01N 15/00*   (2006.01)
  *B01D 46/44*   (2006.01)
  *F01N 3/021*   (2006.01)
(52) U.S. Cl.
  CPC ........ *G01M 15/102* (2013.01); *G01N 1/2252* (2013.01); *B01D 2279/30* (2013.01); *G01M 15/02* (2013.01); *G01N 2001/2255* (2013.01); *G01N 2015/0046* (2013.01)

EXHAUST GAS ANALYSIS SYSTEM, RECORDING MEDIUM RECORDED WITH PROGRAM FOR EXHAUST GAS ANALYSIS SYSTEM, AND EXHAUST GAS ANALYZING METHOD

CROSS-REFERENCE TO RELATED APPLICATION

This application claims priority to JP Application No. 2016-103451, filed May 24, 2016, the disclosure of which is incorporated in its entirety by reference herein.

TECHNICAL FIELD

The present invention relates to an exhaust gas analysis system adapted to analyze, for example, exhaust gas discharged from an engine, a recording medium recorded with a program for the exhaust gas analysis system, and an exhaust gas analyzing method.

BACKGROUND ART

As an exhaust gas analysis system, as disclosed in Patent Literature 1, there has been one using a constant volume sampling apparatus that is configured to sample the total amount of exhaust gas discharged from an internal combustion engine, dilute the totally sampled exhaust gas with diluent gas to produce diluted exhaust gas, and control the flow rate of the diluted exhaust gas to be constant.

Specifically, this system calculates the concentration of a component in the exhaust gas by collecting the diluted exhaust gas into a diluted exhaust gas bag as well as collecting the diluent gas into a diluent gas bag, and subtracting the concentration of the component in the diluent gas in the diluent gas bag from the concentration of the component in the diluted exhaust gas in the diluted exhaust gas bag.

So-called bag measurement adapted to collect diluted exhaust gas and diluent gas into bags as described above is capable of accurately measuring the concentration of a component, but requires many steps before the measurement, such as calibrating an analyzer in order to measure the diluted exhaust gas and the diluent gas, thus taking a long time to obtain a measurement result.

For this reason, when an obtained measurement result is far out of an assumed range and measurement should be repeated, a time required for bag measurement performed by then goes to waste.

In addition, such a problem may occur not only in the case of the bag measurement but also when exhaust gas is introduced to a filter to measure PM or the like contained in the exhaust gas.

Also, one of causes for taking a long time to obtain a measurement result is the presence of a step of temporarily measuring the diluted exhaust gas in the diluted exhaust gas bag before the bag measurement in order to determine a measurement range used to perform the bag measurement for the diluted exhaust gas bag.

In order to omit the step, it is conceivable that a user assumes the concentration of the component in the diluted exhaust gas to set the measurement range of the analyzer in advance. However, in that case, when the concentration of the component in the diluted exhaust gas is different from the assumed one, measurement accuracy may not be ensured.

In such a situation, separately from the above-described bag measurement, the present inventor has focused on a continuous analyzer used to continuously analyze diluted exhaust gas, such as an analyzer used to calculate a fuel consumption in real time, and intensively examined the problem associated with the bag measurement using analysis results by the continuous analyzer.

Citation List

Patent Literature

Patent Literature 1: JP-A 2009-85842

SUMMARY OF INVENTION

Technical Problem

The present invention is made on the basis of the present inventor's intensive examination described above, and the primary object thereof is to improve the efficiency of exhaust gas analysis by using the analysis results by the continuous analyzer to prevent a time spent for measuring exhaust gas introduced to a bag or a filter from being wasted and eliminate the need for a step before bag measurement.

Solution to Problem

That is, an exhaust gas analysis system according to the present invention includes: an exhaust gas circulation line through which exhaust gas flows; an exhaust gas collection line adapted to collect the exhaust gas from the exhaust gas circulation line and introduce the collected exhaust gas into an exhaust gas analysis device; a continuous analysis line adapted to, separately from the exhaust gas collection line, collect the exhaust gas from the exhaust gas circulation line for continuous analysis; a continuous analyzer provided in the continuous analysis line; and an information processing unit adapted to, on the basis of an exhaust gas related value obtained by the continuous analyzer at the time of the collection into the exhaust gas analysis device, determine whether a measurement result of the exhaust gas introduced into the exhaust gas analysis device falls within a preset range, or determine a measurement range used to measure the exhaust gas introduced into the exhaust gas analysis device.

Note that the term "exhaust gas" herein includes raw exhaust gas discharged from an engine and diluted exhaust gas obtained by diluting the raw exhaust gas.

In such an exhaust gas analysis system, since the information processing unit determines, on the basis of the analysis result by the continuous analyzer, whether the measurement result of the exhaust gas introduced into the exhaust gas analysis device such as a bag or a filter falls within the preset range, when the measurement result falls out of the assumed range, analysis can be performed again without measuring the exhaust gas or performing various steps necessary before the measurement. In doing so, when attempting to perform the analysis again, it is possible to prevent wasting of the time required to obtain the measurement result of the exhaust gas introduced into the exhaust gas analysis device, thus improving analysis efficiency.

Also, since the information processing unit determines the measurement range used for the bag measurement on the basis of the analysis result by the continuous analyzer, the need for temporary measurement, which has been performed in the past to determine the measurement range before the bag measurement, can be eliminated. This makes it possible to reduce the number of steps necessary before the bag measurement while appropriately setting the measurement range used for the bag measurement, and therefore analysis efficiency can be improved while ensuring the analysis accuracy of exhaust gas analysis.

Specific embodiments adapted to determine whether the measurement result of the exhaust gas introduced into the exhaust gas analysis device falls within the preset range include one in which the continuous analyzer is one adapted to measure the concentration of a predetermined component contained in the exhaust gas, and the information processing unit includes: an analysis result acquisition part adapted to acquire concentration measured by the continuous analyzer during a predetermined period at the time of the collection into the exhaust gas analysis device; a calculation part adapted to, on the basis of the acquired concentration, calculate as an exhaust gas related value at least one of the average concentration of the predetermined component during the predetermined period, the integrated value of the predetermined component having flowed into the continuous analyzer during the predetermined period, and a fuel consumption during the predetermined period; and a determination part adapted to, on the basis of the exhaust gas related value calculated by the calculation part, determine whether the measurement result of the exhaust gas introduced into the exhaust gas analysis device falls within the preset range.

On the other hand, specific embodiments adapted to determine the measurement range used for the bag measurement include one in which the continuous analyzer is one adapted to measure the concentration of a predetermined component contained in the exhaust gas, and the information processing unit includes: an analysis result acquisition part adapted to acquire concentration measured by the continuous analyzer during a predetermined period at the time of the collection into the exhaust gas analysis device; a calculation part adapted to, on the basis of the acquired concentration, calculate as an exhaust gas related value at least one of the average concentration of the predetermined component during the predetermined period, and the integrated value of the predetermined component having flowed into the continuous analyzer during the predetermined period; and a determination part adapted to, on the basis of the exhaust gas related value calculated by the calculation part, determine the measurement range used to measure the exhaust gas introduced into the exhaust gas analysis device.

It is preferable that the predetermined period is shorter than a period from the start to end of the collection into the exhaust gas analysis device, and before the measurement result of the exhaust gas introduced into the exhaust gas analysis device is obtained, the determination part determines whether the measurement result falls within the preset range.

In such a configuration, since before the completion of the collection into the exhaust gas analysis device, it is determined whether the measurement result of the exhaust gas introduced into the exhaust gas analysis device falls within the preset range, wasted time can be more reduced by discontinuing analysis as necessary without waiting for the completion of the collection into the exhaust gas analysis device.

In the exhaust gas analysis system running a vehicle in multiple preset running modes, and collecting exhaust gas discharged from an engine over the multiple running mode into the exhaust gas analysis device for analysis, it is preferable that the predetermined period is set to a period from the start to end of each of the running modes, and at the end of each of the running modes, the determination part determines whether a measurement result of the exhaust gas introduced into the exhaust gas analysis device falls within the preset range.

In such a configuration, since at the end of each of the running modes, it is determined whether the measurement result of the exhaust gas introduced into the exhaust gas analysis device falls within the preset range, it can be determined at an earlier stage whether the analysis should be discontinued.

As the exhaust gas analysis device, a bag for collecting the exhaust gas or a filter for capturing particulate matter contained in the exhaust gas can be cited.

Also, a recording medium recorded with a program for an exhaust gas analysis system according to the present invention is a recording medium recorded with a program that is used for an exhaust gas analysis system including: an exhaust gas circulation line through which exhaust gas flows; an exhaust gas collection line adapted to introduce the exhaust gas from the exhaust gas circulation line into an exhaust gas analysis device; a continuous analysis line adapted to, separately from the exhaust gas collection line, collect the exhaust gas from the exhaust gas circulation line for continuous analysis; and a continuous analyzer provided in the continuous analysis line, and instructs a computer to, on the basis of an exhaust gas related value obtained by the continuous analyzer at the time of the collection into the exhaust gas analysis device, determine whether a measurement result of the exhaust gas introduced into the exhaust gas analysis device falls within a preset range, or determine a measurement range used to measure the exhaust gas introduced into the exhaust gas analysis device.

Further, the exhaust gas analyzing method according to the present invention is an exhaust gas analyzing method using an exhaust gas analysis system including: an exhaust gas circulation line through which exhaust gas flows; an exhaust gas collection line adapted to collect the exhaust gas from the exhaust gas circulation line and introduce the collected exhaust gas into an exhaust gas analysis device; a continuous analysis line adapted to, separately from the exhaust gas collection line, collect the exhaust gas from the exhaust gas circulation line for continuous analysis; and a continuous analyzer provided in the continuous analysis line, and on the basis of an exhaust gas related value obtained by the continuous analyzer at the time of the collection into the exhaust gas analysis device, the exhaust gas analyzing method determines whether a measurement result of the exhaust gas introduced into the exhaust gas analysis device falls within a preset range, or determines a measurement range used to measure the exhaust gas introduced into the exhaust gas analysis device.

Such a recording medium recorded with a program for an exhaust gas analysis system and exhaust gas analyzing method can produce the same working effect as that of the above-described exhaust gas analysis system.

Advantageous Effects of Invention

According to the present invention configured as described above, the efficiency of exhaust gas analysis can be improved by using an analysis result by the continuous analyzer to prevent the time spent for measuring the exhaust gas introduced into the bag or the filter from being wasted and eliminate the need for steps before the bag measurement.

DESCRIPTION OF EMBODIMENTS

<First Embodiment>

A first embodiment of the exhaust gas analysis system according to the present invention will be described below with reference to drawings.

An exhaust gas analysis system 100 according to the present embodiment is one that is of a dilution sampling type and adapted to dilute engine exhaust gas (hereinafter referred to as "exhaust gas") collected from a vehicle 200 several times with dilution air produced from the atmosphere by purification and then perform concentration measurement. In the present embodiment below, the exhaust gas analysis system 100 of a constant volume dilution sampling type adapted to sample the total amount of the exhaust gas and dilute the sampled exhaust gas with the dilution air to obtain a constant known flow rate will be described.

Figure 1:
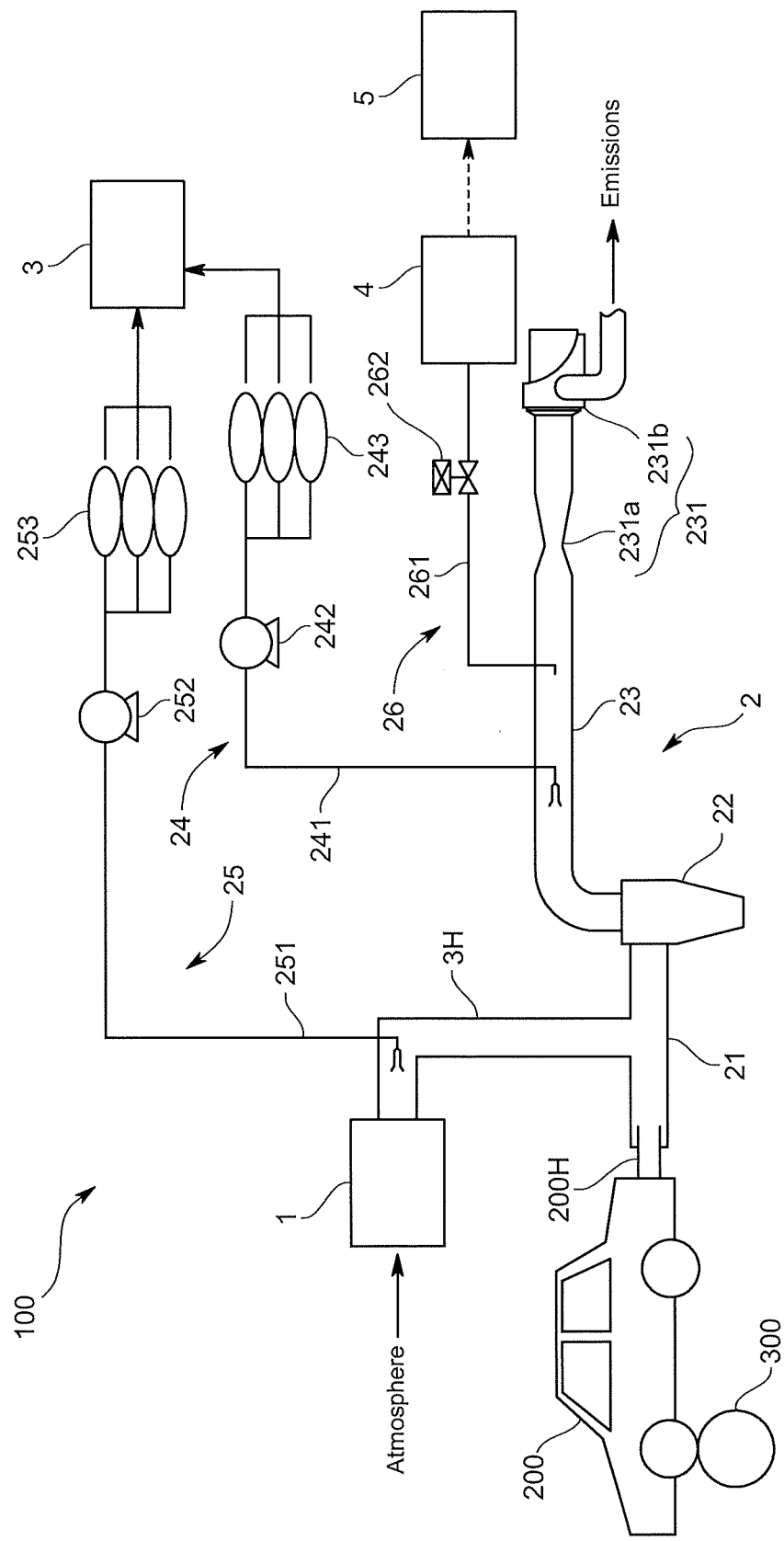
FIG. 1 is a schematic diagram illustrating the overall configuration of an exhaust gas analysis system in a first embodiment.

Specifically, as illustrated in FIG. 1, the exhaust gas analysis system 100 includes: a dilution air take-in part 1 that takes in air in the atmosphere as diluent gas for diluting the exhaust gas; a constant volume sampling apparatus 2 that introduces the total amount of the exhaust gas and the dilution air thereinto to control the total flow rate of them to be constant, and collects part of the exhaust gas diluted (hereinafter referred to as "diluted exhaust gas") into a collection bag at a constant flow rate; a gas analysis apparatus 3 that analyzes the concentration of a predetermined component in the diluted exhaust gas collected into the collection bag of the constant volume sampling apparatus 2; and a continuous analyzer 4 that continuously analyzes the predetermined component in the diluted exhaust gas separately from the gas analysis apparatus 3.

The constant volume sampling apparatus 2 includes: an exhaust gas introduction line 21 that is connected to an exhaust pipe 200H of the vehicle 200 mounted on a chassis dynamometer 300 and introduced and connected with a dilution air supply pipe 311 of the dilution air take-in part 1; a cyclone 22 that is provided downstream of the exhaust gas introduction line 21 to stir and mix the exhaust gas and the dilution air; a diluted exhaust gas circulation line 23 that has a constant flow rate mechanism 231 adapted to, at a constant flow rate, flow the diluted exhaust gas resulting from the stirring and mixing by the cyclone 22; a diluted exhaust gas collection line 24 for collecting the diluted exhaust gas from the diluted exhaust gas circulation line 23; a dilution air collection line 25 for collecting the dilution air from the dilution air supply pipe 3H; and a continuous analysis line 26 for collecting the diluted exhaust gas from the diluted exhaust gas circulation line 23 to continuously analyze the collected diluted exhaust gas.

The constant flow rate mechanism 231 is configured to include a venturi pipe 231a provided in the diluted exhaust gas circulation line 23 and a turbo blower 231b provided downstream of the venturi tube 231a.

The diluted exhaust gas collection line 24 includes: a diluted exhaust gas collection pipe 241 of which one end is provided inside the diluted exhaust gas circulation line 23; a diluted exhaust gas collection pump 242 provided in the diluted exhaust gas collection pipe 241; and diluted exhaust gas bags 243 as exhaust gas analysis devices adapted to contain the diluted exhaust gas collected by the diluted exhaust gas collection pump 242. At the one end of the diluted exhaust gas collection line 24, a flow rate control part (e.g., a venturi) for controlling a collection flow rate is provided. Note that the diluted exhaust gas collection pipe 241 is provided on the upstream side of the constant flow rate mechanism 231.

Also, the dilution air collection line 25 includes: a dilution air collection pipe 251 of which one end is provided inside the dilution air supply pipe 3H; a dilution air collection pump 252 provided in the dilution air collection pipe 251; and dilution air bags 253 as exhaust gas analysis devices adapted to contain the dilution air collected by the dilution air collection pump 252. At the one end of the dilution air collection line 25, a flow rate control part (e.g., a venturi) for controlling a collection flow rate is provided.

In addition, using the diluted exhaust gas bags 243 of the diluted exhaust gas collection line 24 and the dilution air bags 253 of the dilution air collection line 25, the gas analysis apparatus 3 performs so-called bag measurement.

The gas analysis apparatus 3 measures the concentrations of predetermined components (hereinafter also referred to as component concentrations) such as CO, $CO_2$, NO, and THC contained in the diluted exhaust gas in the diluted exhaust gas bags 243 and in the dilution air in the dilution air bags 253, and has one or more analyzers adapted to detect these components and an arithmetic calculation unit.

The analyzers are ones such as infrared gas analyzers that uses a non-dispersive infrared absorption method (NDIR) to measure the concentrations of CO, $CO_2$, NO, and the like, a THC meter that uses a heating type hydrogen flame ionization detecting method (HFID) to measure the concentration of THC, and a $CH_4$ meter that uses a gas chromatograph/hydrogen flame ionization detector (GC-FID) to measure the concentration of $CH_4$.

The arithmetic calculation unit physically includes a CPU, a memory, an A/D converter, a communication interface, and the like, and fulfills a function as a calculation part that makes background corrections to calculate the concentrations of the components contained in the exhaust gas by acquiring output values from the analyzers and subtracting the concentrations of the components contained in the dilution air from the concentrations of the components contained in the diluted exhaust gas, correspondingly.

The continuous analysis line 26 includes: a diluted exhaust gas collection pipe 261 of which one end is provided inside the diluted exhaust gas circulation line 23; and an on-off valve 262 provided in the diluted exhaust gas collection pipe 261. The continuous analysis line 26 is provided with the continuous analyzer 4 to make it possible to introduce the diluted exhaust gas into the continuous analyzer 4 by an unillustrated pump in the continuous analysis line 26 and continuously analyze the diluted exhaust gas. The one end of the continuous analysis line 26 may be on the upstream or downstream side of the one end of the diluted exhaust gas collection line 24, and in the present embodiment, is provided on the downstream side.

The continuous analyzer 4 is one adapted to measure at least the component concentrations to be measured by the above-described gas analysis apparatus 3, and capable of obtain measurement results in a shorter time than bag measurements to be made by the gas analysis apparatus 3. That is, the continuous analyzer 4 in the present embodiment is one adapted to measure the concentrations of the components such as CO, $CO_2$, NO, and THC contained in the diluted exhaust gas, and specifically, includes analyzers such as infrared gas analyzers that uses a non-dispersive infrared absorption method (NDIR) to measure the concentrations of CO, $CO_2$, NO, and the like, a THC meter that uses a heating type hydrogen flame ionization detecting method (HFID) to measure the concentration of THC, and a $CH_4$ meter that uses a gas chromatograph/hydrogen flame ionization detector (GC-FID) to measure the concentration of $CH_4$.

The continuous analyzer 4 in the present embodiment is configured to, at least during a preset predetermined period, continuously analyze the component concentrations of the diluted exhaust gas introduced into the continuous analyzer 4 and also successively output component concentration signals indicating the instantaneous values of the component concentrations as analysis results.

Note that the present embodiment is adapted to share the common analyzers between the continuous analyzer 4 and the gas analysis apparatus 3 by switching lines respectively connected to the analyzers to the diluted exhaust gas collection line 24, dilution air collection line 25, or continuous analysis line 26. Of course, the analyzers of the continuous analyzer 4 and those of the gas analysis apparatus 3 may be different from each other.

In addition, the exhaust gas analysis system 100 of the present embodiment further includes an information processing unit 5 that on the basis of analysis results obtained by the continuous analyzer 4 at the time of collection into the diluted exhaust gas bags 243, determines whether results of making the bag measurements of the diluted exhaust gas in the diluted exhaust gas bags 243 (hereinafter also referred to as bag measurement results) fall within preset ranges, correspondingly.

Note that the term "preset ranges" refers to ranges within which when the bag measurements are normally made, the resulting results are assumed to fall by a user (hereinafter also referred to as assumed ranges).

Figure 2:
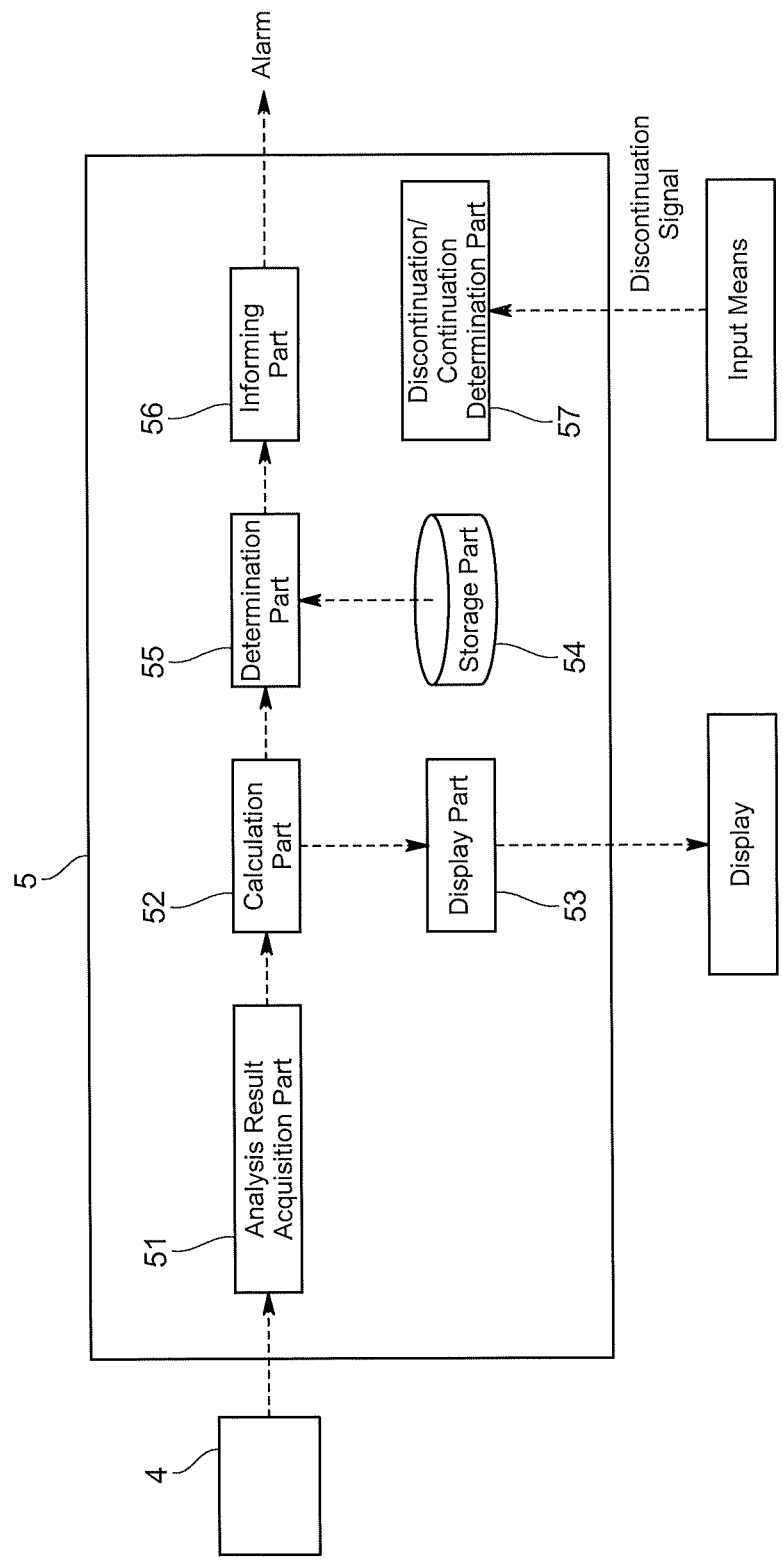
FIG. 2 is a functional block diagram illustrating the functions of an information processing unit in the first embodiment.

Specifically, the information processing unit 5 physically includes a CPU, a memory, an A/D converter, a communication interface, and the like, and functionally, as illustrated in FIG. 2, includes an analysis result acquisition part 51, a calculation part 52, a display part 53, a storage part 54, a determination part 55, and an informing part 56.

These respective parts are implemented by the cooperation of the CPU and its peripheral devices performed in accordance with a program stored in the memory. In the following, the respective parts will be described.

The present embodiment describes the case where for analysis, the diluted exhaust gas and the dilution air are collected into the diluted exhaust gas bags 243 and dilution air bags 253 that are different for each of multiple phases such as a cold start phase, transient phase, and hot start phase, like the case of the FTP-75 test procedure.

Note that a time to run the vehicle in each of the phases, i.e., a time to collect the diluted exhaust gas and the dilution air into the respective bags 243 and 253 in each of the phases is preset.

The analysis result acquisition part 51 acquires the component concentration signals successively outputted from the continuous analyzer 4 by, for example, wire or wireless, and successively transmits the component concentrations indicated by the component concentration signals to the calculation part 52.

The calculation part 52 is one adapted to calculate exhaust gas related values on the basis of the component concentrations transmitted from the analysis result acquisition part 51, and in the present embodiment, as the exhaust gas related values, calculates the integrated values of the predetermined components having flowed into the continuous analyzer 4 during the predetermined period at the time of collection into the diluted exhaust gas bags 243. Note that the integrated values are calculated on the basis of the concentrations and the exhaust gas flow rate (in the present embodiment, the diluted exhaust gas flow rate).

The predetermined period is set to a period from the start to end of each phase, i.e., to a period from the start to collect the diluted exhaust gas and the dilution air into the diluted exhaust gas bags 243 and the dilution air bags 253 to the completion of the collection in each phase.

Figure 3:
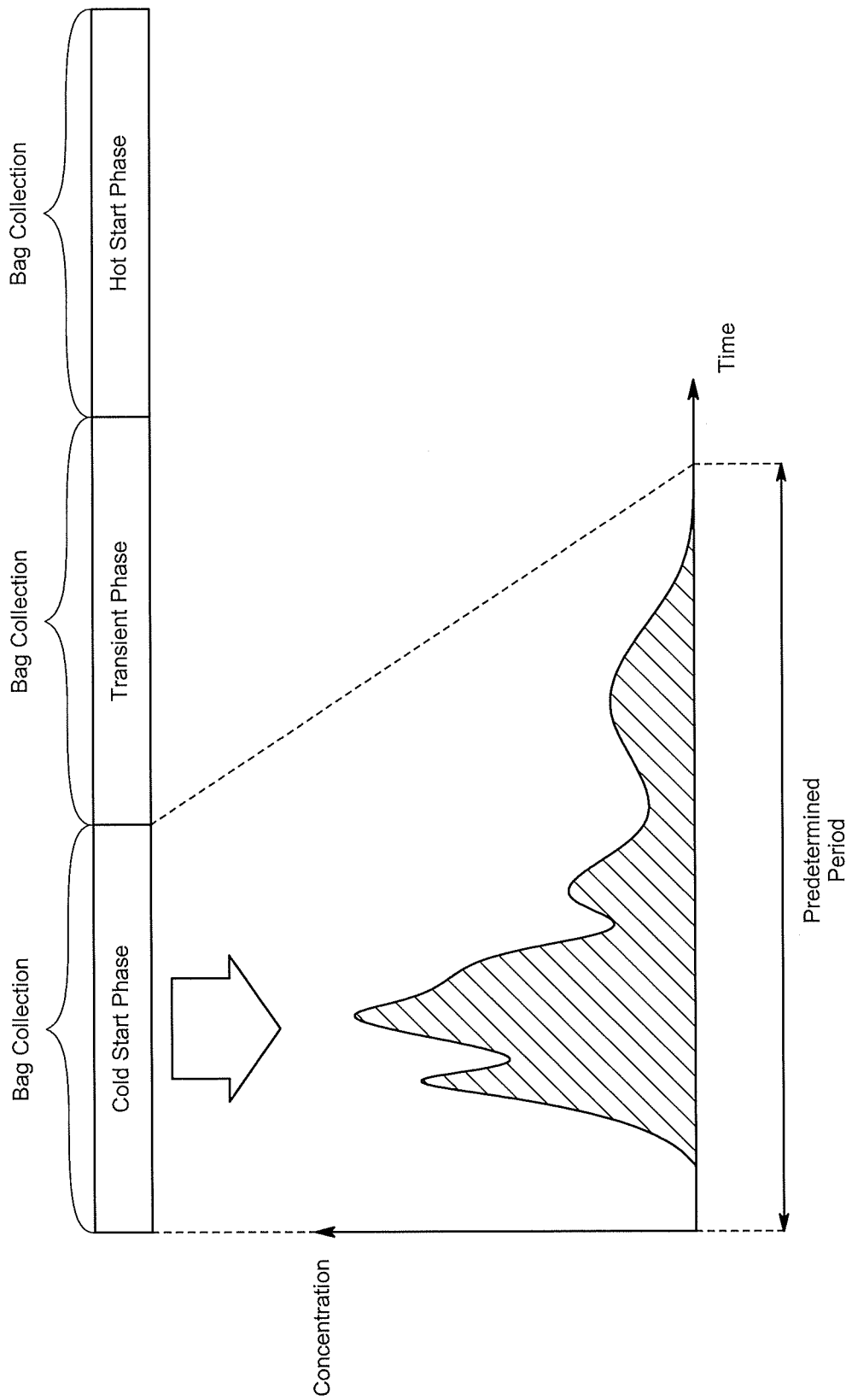
FIG. 3 is a diagram for explaining setting of a predetermined period in the first embodiment.

To describe this more specifically, as illustrated in FIG. 3, when a component concentration obtained by the continuous analyzer 4 during a period from the start to end of one phase (e.g., the cold start phase) varies, the calculation part 52 integrates the product of the instantaneous value of the component concentration and the exhaust gas flow rate during this period, and thereby calculates an integrated value. Note that the integrated value may be calculated by multiplying the average value of the component concentration during the predetermined period by the total exhaust gas flow rate.

The display part 53 is one adapted to output the calculation results for display on, for example, a display or the like, and in the present embodiment, displays the integrated values calculated by the calculation part 52 after the end of each phase.

The storage part 54 is set in a predetermined area of the memory, and stores reference values for determining whether the bag measurement results fall within the assumed ranges, correspondingly.

The reference values refer to ranges preset by a user on the basis of the assumed ranges, and in the present embodiment, reference values corresponding each phase are stored in the storage part 54.

Specifically, the reference values are set such that when the integrated values calculated by the calculation part 52 are equal to or more than the reference values, the bag measurement results fall within the assumed ranges, whereas when the integrated values are larger than the reference values, the bag measurement results fall out of the assumed ranges, correspondingly. Note that as a cause for any of the integrated values larger than a corresponding reference value, one such as the failure or deterioration of a catalyst installed in the exhaust pipe 200H of the vehicle 200 is conceivable.

The determination part 55 acquires and compares the integrated value calculated by the calculation part 52 and the reference values stored in the storage part 54 to determine whether the bag measurement results fall within the assumed ranges, correspondingly.

That is, the determination part 55 in the present embodiment is configured to, on the basis of the magnitude relationships between the integrated values and the reference values, determine whether the bag measurement results fall within the assumed ranges, correspondingly. In other words, when the integrated values are equal to or less than the reference values, the determination part 55 determines that the bag measurement results fall within the assumed ranges, and when the integrated values are larger than the reference values, determines that the bag measurement results do not fall within the assumed ranges, correspondingly.

When the determination part 55 determines that any of the bag measurement results does not fall within a corresponding assumed range, i.e., when any of the integrated values is larger than a corresponding reference value, the informing part 56 outputs an alarm to inform a user of that. Specific methods for outputting the alarm include ones such as a method adapted to display a warning on the display or the like and a method adapted to inform the user by some means such as sound or light.

Figure 4:
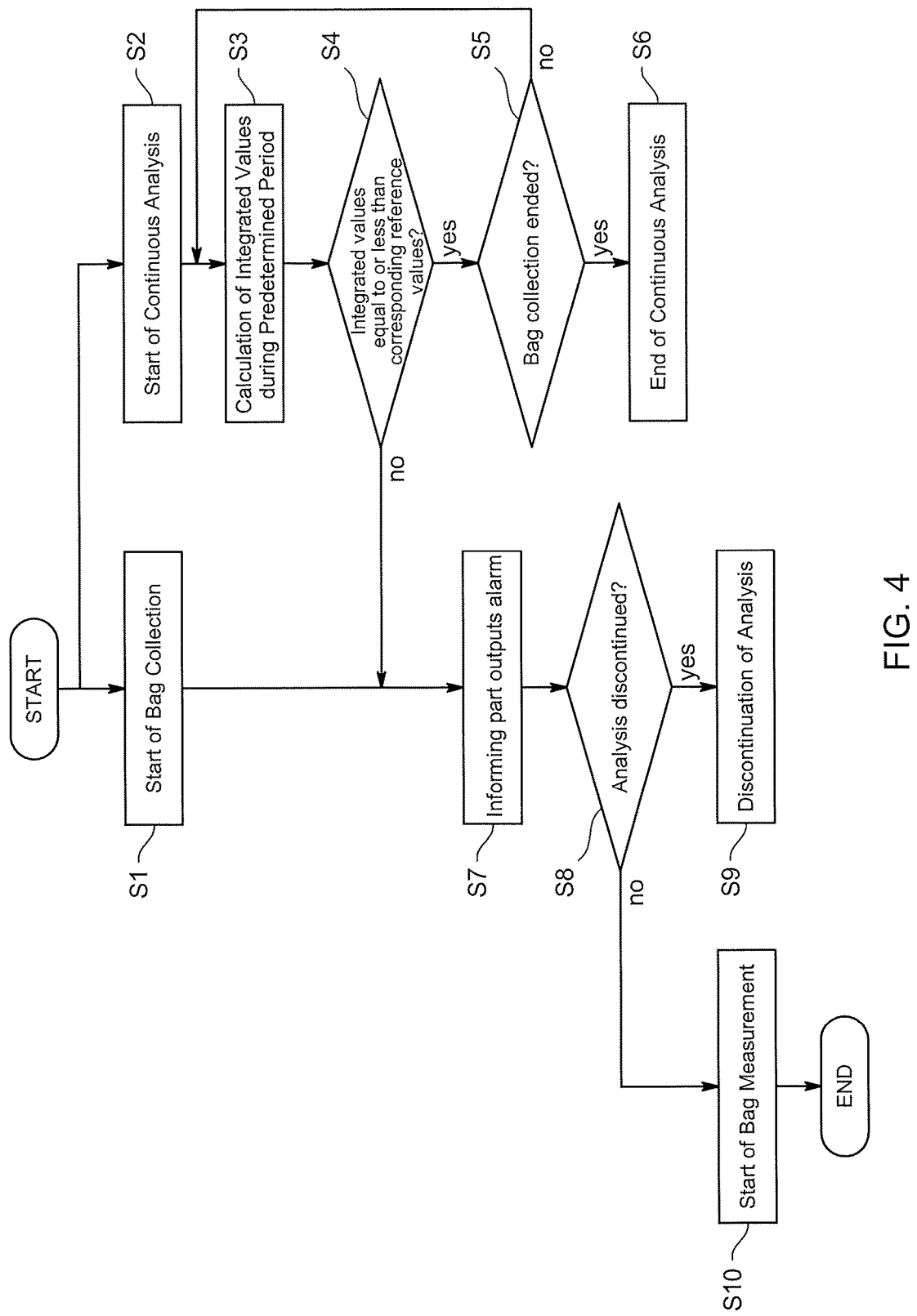
FIG. 4 is a flowchart illustrating the actions of the exhaust gas analysis system in the first embodiment.

Subsequently, the actions of the exhaust gas analysis system 100 of the present embodiment will be described with reference to a flowchart of FIG. 4.

First, when exhaust gas analysis is started, a preparation for stabilizing a state of the vehicle is made, and then in the present embodiment, the cold start phase as a first phase is started.

When the first phase is started, the diluted exhaust gas and the dilution air are collected into the diluted exhaust gas bags 243 and the dilution air bags 253 (hereinafter also referred to as bag collection) (S1) and at the same time, the on-off valve 262 is opened to start continuous analysis (S2).

Then, after the predetermined period has passed, i.e., after the completion of the bag collection in the first phase, the calculation part 52 calculates the integrated values of the predetermined components during the predetermined period (S3).

Subsequently, the determination part 55 compares the calculated integrated values and reference values corresponding to the first phase to determine whether the integrated values are equal to or less than the referenced values, correspondingly (S4).

When the integrated values are equal to or less than the reference values, the information processing unit 5 determines whether the bag collection in the next phase (in the present embodiment, the transient phase) is performed. i.e., whether the diluted exhaust and the dilution air are collected into diluted exhaust gas bags 243 and dilution air bags 253 different from those in the first phase (S5). When the bag collection still continues, the flow returns to S3 again, whereas when the bag collection is ended, the continuous analysis is ended (S6).

On the other hand, in S4, when any of the integrated values is larger than a corresponding reference value, the informing part 56 provides this information (S7).

Meanwhile, the information processing unit 55 in the present embodiment is configured to be capable of inputting a discontinuation signal indicating that a user discontinues the analysis using input means, and a discontinuation/continuation determination part 57 illustrated in FIG. 2 determines on the basis of the presence or absence of the discontinuation signal whether to discontinue or continue the analysis (S8).

When the discontinuation/continuation determination part 57 receives the discontinuation signal, the bag collection performed at the time is discontinued to discontinue the exhaust gas analysis (S9).

On the other hand, when the discontinuation/continuation determination part 57 does not receive the discontinuation signal, the bag measurement to be performed on the diluted exhaust gas bags 243 and the dilution air bags 253 are started (S10), and when the bag measurement is ended, the current phase is ended.

After that, when the next phase still remains, the flow returns to S1.

In the exhaust gas analysis system 100 according to the present embodiment configured as described above, since it is determined on the basis of analysis results by the continuous analyzer 4 whether results of bag measurement fall within the assumed ranges, correspondingly, when it is determined that any of the measurement results falls out of a corresponding assumed range, analysis can be performed again without performing the bag measurement and various steps required before the bag measurement. In doing so, wasted bag measurement and the like can be avoided As a result, the time required to obtain bag measurement results can be prevented from being wasted, and thereby analysis efficiency can be improved.

In addition, since the display part 53 outputs calculation results by the calculation part 52 for display on the display or the like, independently of a determination result by the determination part 55, a user can determine on the basis of values displayed by the display part 53 whether bag measurement results correspondingly fall within the assumed range.

Further, since the predetermined time is set to a period from the start to end of each phase, in particular, in the first phase (the cold start phase) where any of the bag measurement results is likely to fall out of a corresponding assumed range, it can be determined whether the bag measurement results correspondingly fall within the assumed ranges, and when any of the bag measurement results is determined to fall out of a corresponding assumed range, it can be prevented to spend wasted time for the subsequent phase.

<Variations of First Embodiment>

Note that the present invention is not limited to the above-described first embodiment.

For example, the above-described embodiment describes the case where, for each of the multiple phases, the diluted exhaust gas and the dilution air are collected into different bags and analyzed. However, the exhaust gas analysis system may be a system adapted to, as prescribed in the 10-15 mode exhaust gas test of TRIAS, run the vehicle in multiple predetermined running modes, and dilute the exhaust gas discharged from the engine over these multiple running modes with the dilution air to collect the diluted exhaust gas into the bags.

In this case, the predetermined period may be set to a period from the start to completion of the bag collection as in the above-described embodiment, however, it may be configured to set the predetermined period to a period shorter than that period, and before the completion of the bag collection, make the determination part determine whether bag measurement results correspondingly fall within the assumed ranges.

Figure 5:
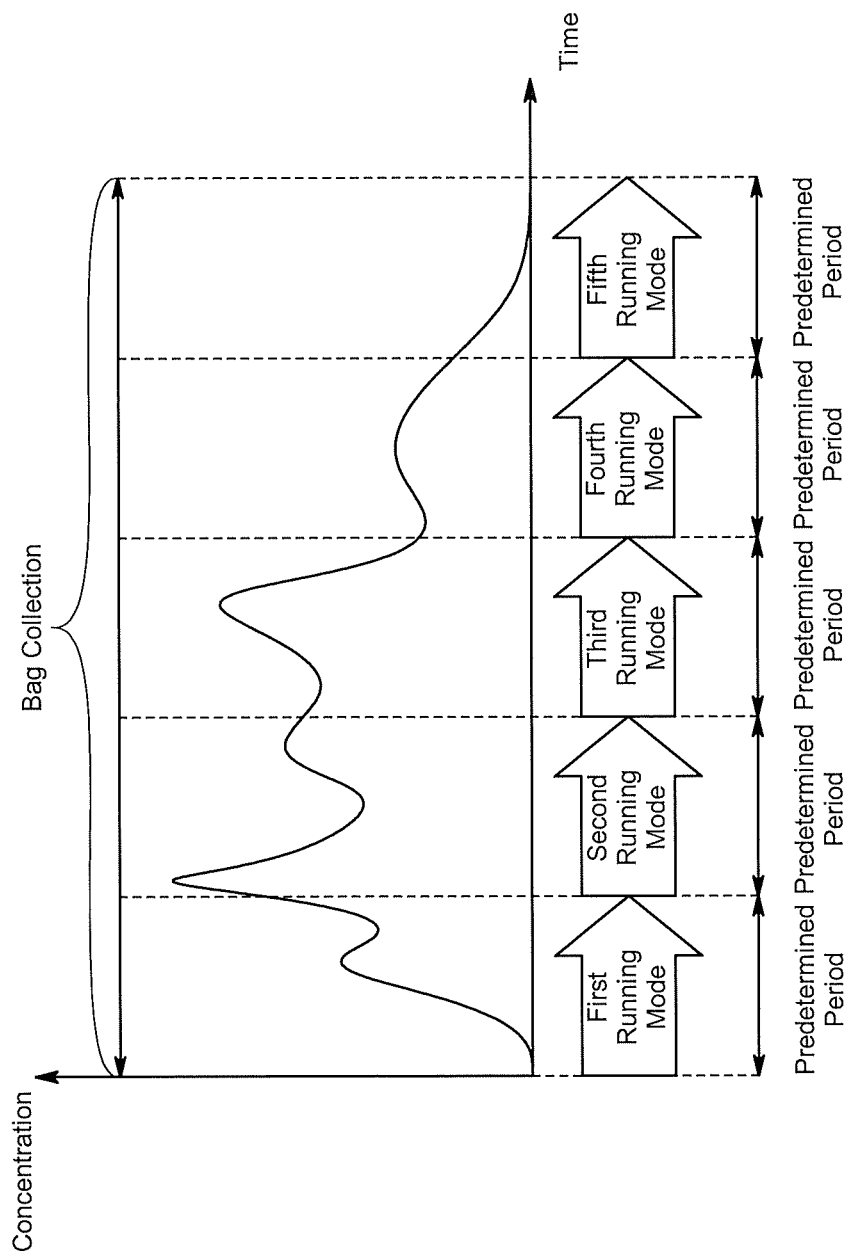
FIG. 5 is a diagram for explaining setting of a predetermined period in a variation of the first embodiment.

More specifically, for example, as illustrated in FIG. 5, the predetermined period may be set to a period from the start to end of each of running modes. In addition, a period from the start to end of a running mode may be set to have a different length or the same length among the running modes.

Such a configuration makes it possible to, at the end of each of the running modes, determine on the basis of analysis results obtained by the continuous analyzer in that running mode whether bag measurement results correspondingly fall within the assumed range, and therefore it can be determined at an early stage whether bag measurement should be continued or discontinued.

Figure 6:
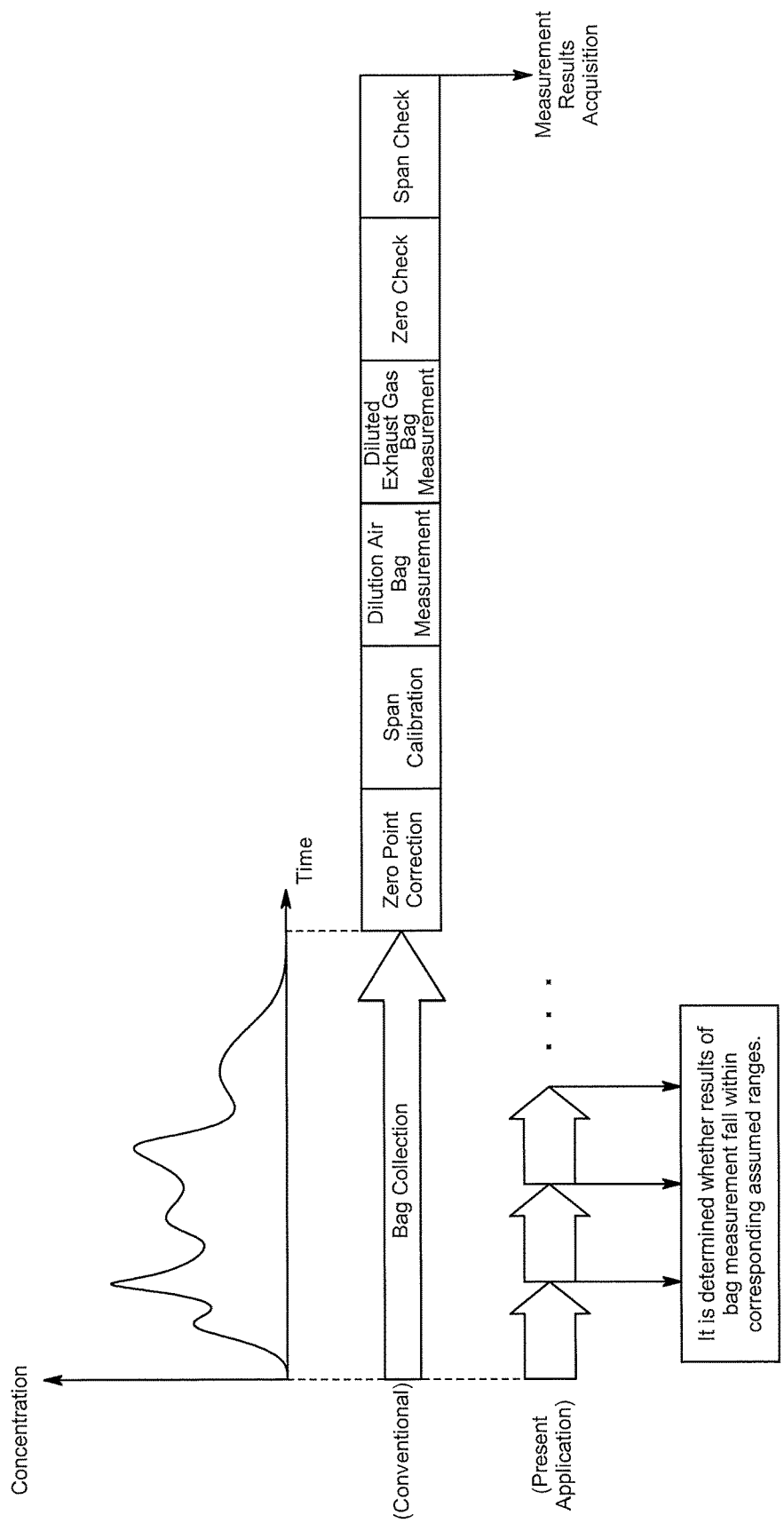
FIG. 6 is a diagram for explaining the effect of the variation of the first embodiment.

To describe this more specifically, as illustrated in FIG. 6, it is conventionally adapted to collect the diluted exhaust gas and the dilution air respectively into the diluted exhaust gas bags and the dilution air bags, then perform zero point correction, span calibration, measurement on each bag, zero check, and span check, and after the completion of these steps, obtain bag measurement results. For this reason, when any of the bag measurement results does not fall within a corresponding assumed range, and the measurement is attempted to be performed again, the time required for the above-described various steps is wasted.

On the other hand, in the above-described configuration of the present application, as illustrated in FIG. 6, since before the completion of the bag collection, it is determined on the basis of analysis results by the continuous analyzer whether bag measurement results correspondingly fall within the assumed ranges, wasted time can be drastically reduced more than before by discontinuing analysis as necessary without waiting for the completion of the collection into the exhaust gas analysis devices and without performing the above-described respective steps.

In addition, the calculation part in the above-described embodiment calculates the integrated values of the predetermined components during the predetermined period as the exhaust gas related values, but may be one adapted to, as the exhaust gas related values, calculate the average concentrations of the predetermined components during the predetermined period and/or a fuel consumption during the predetermined period obtained by a carbon balance method.

In either case, it is only necessary that reference values for determining whether bag measurement results correspondingly fall within the assumed ranges are stored in the storage part so as to correspond to the parameters calculated by the calculation part.

Further, for example, as illustrated in FIG. 5, when the predetermined period is shorter than the period from the start to end of the bag collection, the calculation part may sequentially and correspondingly sum up, for example, integrated values calculated during each predetermined period. That is, the calculation part may be adapted to, every time a predetermined period passes, calculate integrated values from the start of the bag collection until that predetermine period passes.

In addition, the storage part in the above-described embodiment stores reference values for determining whether bag measurement results correspondingly fall within the assumed ranges, but may store, instead of the reference values, reference ranges defined by the upper and lower limit values, correspondingly.

In this case, it is only necessary that the determination part is configured to determine, on the basis of whether integrated values calculated by the calculation part fall within reference ranges, whether bag measurement results fall within the assumed ranges, correspondingly.

Further, the above-described embodiment is adapted to determine whether bag measurement results correspondingly fall within the assumed ranges, but may be adapted to determine the bag measurement results correspondingly fall within ranges determined as, for example, limit values.

Still further, in the above-described embodiment, the exhaust gas analysis devices are the diluted exhaust gas bags and the dilution air bags; however, a filter provided in the diluted exhaust gas collection line to capture particulate matter (PM) contained in the exhaust gas may be used as an exhaust gas analysis device.

In this case, as the continuous analyzer, one capable of obtaining a measurement result in a shorter time than that required for PM measurement using the filter, and continuously measuring particulate matter, such as a diffusion charger (DC) or a CPC, can be cited.

In such a configuration, since before the completion of capturing PM by the filter, it can be determined whether a result of the PM measurement falls within a preset range, wasted time can be more reduced by discontinuing analysis as necessary without waiting for the completion of the capturing by the filter.

<Second Embodiment>

Next, an exhaust gas analysis system according to a second embodiment will be described.

In the second embodiment, an information processing unit is different in function and action from that in the first embodiment, and this will be described below.

Figure 7:
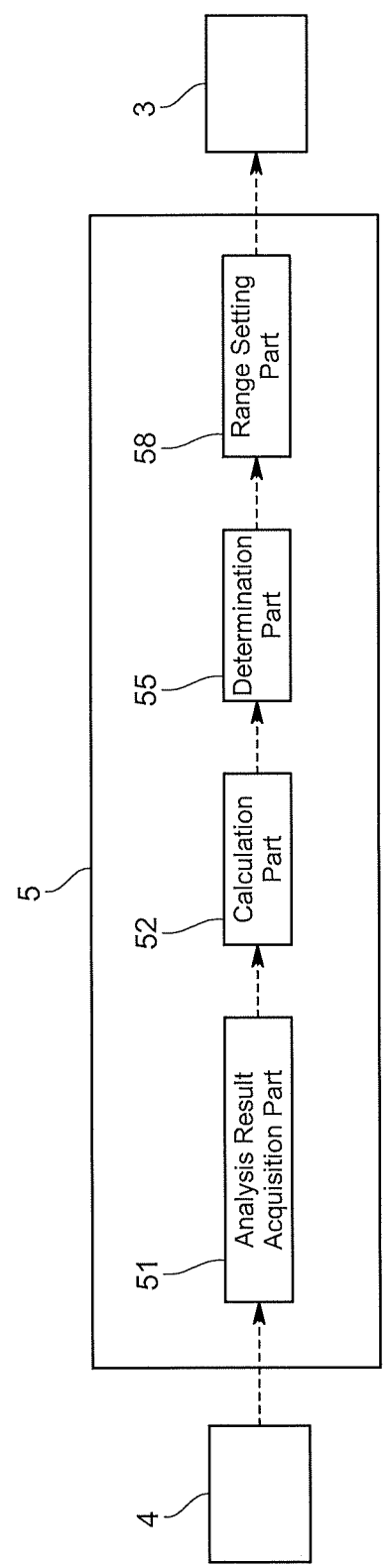
FIG. 7 is a functional block diagram illustrating the functions of an information processing unit in a second embodiment.

As illustrated in FIG. 7, the information processing unit in the present embodiment includes an analysis result acquisition part 51, calculation part 52, determination part 55, and range setting part 58.

The respective parts will be described below.

As in the first embodiment, the analysis result acquisition part 51 acquires component concentration signals successively outputted from a continuous analyzer 4 by, for example, wire or wireless, and successively transmits component concentrations indicated by the component concentration signals to the calculation part 52.

The calculation part 52 calculates the average concentrations of predetermined components during a predetermined period on the basis of the component concentrations transmitted from the analysis result acquisition part 51.

The predetermined period in the present embodiment is a period from the start to collect diluted exhaust gas and dilution air into diluted exhaust gas bags 243 and dilution air bags 253 to the completion of the collection.

The determination part 55, on the basis of the average concentrations calculated by the calculation part 52, determines measurement ranges used for bag measurement, and is configured to, for example, from multiple levels of preset measurement ranges, select optimum ones.

The range setting part 58 outputs range signals indicating the measurement ranges determined by the determination part 55 to a gas analysis apparatus 3.

Figure 8:
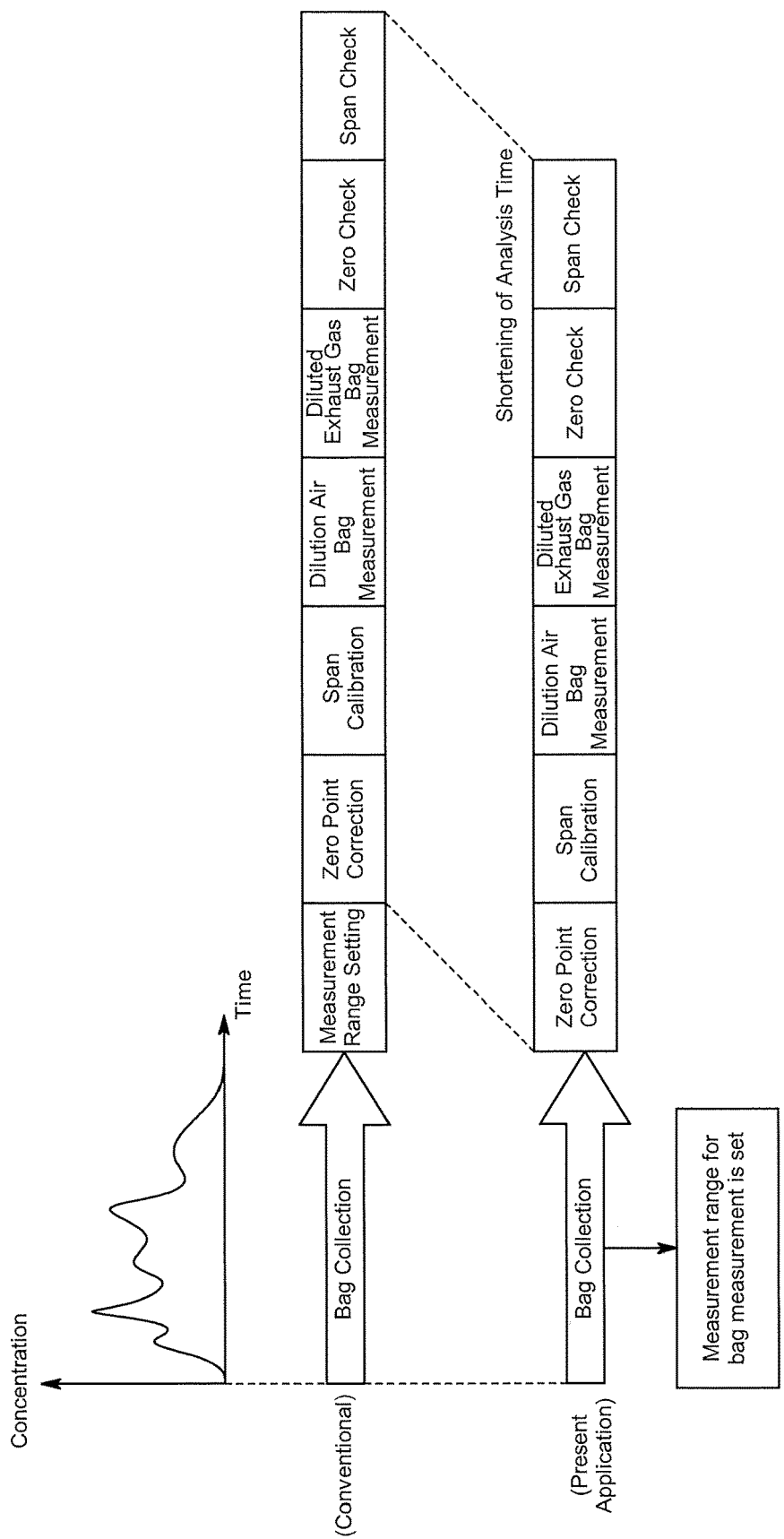
FIG. 8 is a diagram for explaining the effect of the second embodiment.

In the exhaust gas analysis system 100 configured as described above, since on the basis of the average concentrations calculated by the calculation part 52, the determination part 55 determines the measurement ranges used for the bag measurement, and the range setting part 58 sets the measurement ranges for the gas analysis apparatus 3, as illustrated in FIG. 8, the need for temporary measurement before the bag measurement, which has been performed to determine the measurement ranges in the past, can be eliminated. This makes it possible to reduce the number of steps necessary before the bag measurement while appropriately setting the measurement ranges used for the bag measurement, and therefore it is possible to shorten analysis time and improve analysis efficiency while ensuring the analysis accuracy of exhaust gas analysis.

Further, when measurement ranges used for one type of bag measurement and measurement ranges used for another type of bag measurement, both of which are determined by the determination part 55, are the same, the settings and the like of the gas analysis apparatus 3 used for these types of bag measurement can be made common. This makes it possible to, for example, after calibrating the gas analysis apparatus 3 for performing the one type of bag measurement, omit the calibration of the gas analysis apparatus 3 for performing the other type of bag measurement, and therefore analysis efficiency can be more improved.

<Variations of Second Embodiment>

Note that the present invention is not limited to the above-described second embodiment.

For example, the calculation part in the above-described embodiment is one adapted to calculate the average concentrations of the predetermined components during the predetermined period, but may be one adapted to calculate the integrated values of the predetermined components during the predetermined period.

Also, as in the first embodiment, the information processing unit may include a display part adapted to output calculation results calculated by the calculation part for display on a display or the like.

In doing so, independently of a determination result by the determination part, a user can determine measurement ranges used for bag measurement on the basis of values displayed by the display part.

<Other Variations>

The present invention is not limited to any of the above-described embodiments and variations.

For example, the information processing unit may be one including both of the functions in the first embodiment and the functions in the second embodiment. That is, the information processing unit may be configured to, on the basis of analysis results by the continuous analyzer, determine measurement ranges used for bag measurement as well as determining whether bag measurement results correspondingly fall within the assumed ranges.

Any of the above-described embodiments and variations is adapted to take in air in the atmosphere as the diluent gas, but may use a dilution air purifier for producing the dilution air as the diluent gas by purification.

Also, the exhaust gas system in any of the above-described embodiments and variations uses the constant volume sampling apparatus, but may use a bag mini-diluter for collecting part of the exhaust gas to dilute the collected exhaust gas at a certain ratio.

Besides, it should be appreciated that the present invention is not limited to any of the above-described embodiment and variations, but can be variously modified without departing from the scope thereof.

REFERENCE SIGNS LIST

100: Exhaust gas analysis system
23: Diluted exhaust gas circulation line
24: Diluted exhaust gas collection line
26: Continuous analysis line
3: Gas analysis apparatus
4: Continuous analyzer
5: Information processing unit

The invention claimed is:

1. An exhaust gas analysis system comprising:
    an exhaust gas circulation line through which exhaust gas flows;
    an exhaust gas collection line configured to collect the exhaust gas from the exhaust gas circulation line and introduce the collected exhaust gas into an exhaust gas analysis device;
    a continuous analysis line configured to, separately from the exhaust gas collection line, collect the exhaust gas from the exhaust gas circulation line for continuous analysis;
    a continuous analyzer provided in the continuous analysis line and configured to measure concentration of a predetermined component contained in the exhaust gas; and
    an information processing unit comprising
        an analysis result acquisition part configured to acquire concentration measured by the continuous analyzer during a predetermined period at a time of the collection into the exhaust gas analysis device,
        a calculation part configured to calculate an exhaust gas related value using the acquired concentration, wherein the exhaust gas related value is an average concentration of the predetermined component during the predetermined period, an integrated value of the predetermined component having flowed into the continuous analyzer during the predetermined period, or a fuel consumption during the predetermined period, and
        a determination part configured to, by comparing the exhaust gas related value to a reference value, determine whether a measurement result of the exhaust gas introduced into the exhaust gas analysis device falls within a preset range.

2. The exhaust gas analysis system according to claim 1, wherein
    the predetermined period is shorter than a period from a start of the collection into the exhaust gas analysis device to an end of the collection, and
    before the measurement result of the exhaust gas introduced into the exhaust gas analysis device is obtained, the determination part determines whether the measurement result falls within the preset range.

3. The exhaust gas analysis system according to claim 2,
    the exhaust gas analysis system running a vehicle in multiple preset running modes, and collecting exhaust gas discharged from an engine over the running modes into the exhaust gas analysis device for analysis, wherein
    the predetermined period is set to a period from a start of each of the running modes to an end of that running mode, and
    at an end of each of the running modes, the determination part determines whether a measurement result of the exhaust gas introduced into the exhaust gas analysis device falls within the preset range.

4. The exhaust gas analysis system according to claim 1, wherein
    the exhaust gas analysis device is a bag for collecting the exhaust gas or a filter for capturing particulate matter contained in the exhaust gas.

5. An exhaust gas analyzing method using an exhaust gas analysis system comprising an exhaust gas circulation line through which exhaust gas flows, an exhaust gas collection line configured to collect the exhaust gas from the exhaust gas circulation line and introduce the collected exhaust gas into an exhaust gas analysis device, a continuous analysis line configured to, separately from the exhaust gas collection line, collect the exhaust gas from the exhaust gas circulation line for continuous analysis, a continuous analyzer provided in the continuous analysis line and configured to measure concentration of a predetermined component contained in the exhaust gas, and an information processing unit, the exhaust gas analyzing method comprising:

by the information processing unit,
acquiring concentration measured by the continuous analyzer during a predetermined period at a time of the collection into the exhaust gas analysis device,
calculating an exhaust gas related value using the acquired concentration, wherein the exhaust gas related value is an average concentration of the predetermined component during the predetermined period, an integrated value of the predetermined component having flowed into the continuous analyzer during the predetermined period, or a fuel consumption during the predetermined period, and
determining whether a measurement result of the exhaust gas introduced into the exhaust gas analysis device falls within a preset range by comparing the exhaust gas related value to a reference value.

6. An exhaust gas analysis system comprising:
an exhaust gas circulation line through which exhaust gas flows;
an exhaust gas collection line configured to collect the exhaust gas from the exhaust gas circulation line and introduce the collected exhaust gas into an exhaust gas analysis device;
a continuous analysis line configured to, separately from the exhaust gas collection line, collect the exhaust gas from the exhaust gas circulation line for continuous analysis;
a continuous analyzer provided in the continuous analysis line and configured to measure concentration of a predetermined component contained in the exhaust gas; and
an information processing unit comprising
an analysis result acquisition part configured to acquire concentration measured by the continuous analyzer during a predetermined period at a time of the collection into the exhaust gas analysis device,
a calculation part configured to calculate an exhaust gas related value using the acquired concentration, wherein the exhaust gas related value is an average concentration of the predetermined component during the predetermined period, or an integrated value of the predetermined component having flowed into the continuous analyzer during the predetermined period, and
a determination part configured to determine, from the exhaust gas related value, a measurement range used to measure the exhaust gas introduced into the exhaust gas analysis device.

7. An exhaust gas analyzing method using an exhaust gas analysis system comprising an exhaust gas circulation line through which exhaust gas flows, an exhaust gas collection line configured to collect the exhaust gas from the exhaust gas circulation line and introduce the collected exhaust gas into an exhaust gas analysis device, a continuous analysis line configured to, separately from the exhaust gas collection line, collect the exhaust gas from the exhaust gas circulation line for continuous analysis, a continuous analyzer provided in the continuous analysis line and configured to measure concentration of a predetermined component contained in the exhaust gas, and an information processing unit, the exhaust gas analyzing method comprising:
by the information processing unit,
acquiring concentration measured by the continuous analyzer during a predetermined period at a time of the collection into the exhaust gas analysis device,
calculating an exhaust gas related value using the acquired concentration, wherein the exhaust gas related value is an average concentration of the predetermined component during the predetermined period, or an integrated value of the predetermined component having flowed into the continuous analyzer during the predetermined period, and
determining, from the exhaust gas related value, a measurement range used to measure the exhaust gas introduced into the exhaust gas analysis device.

\* \* \* \* \*